United States Patent
Almarzooq et al.

(10) Patent No.: US 11,078,785 B1
(45) Date of Patent: Aug. 3, 2021

(54) REAL-TIME WELL DRILLING EVALUATION SYSTEMS AND METHODS

(71) Applicant: Saudi Arabian Oil Company, Dhahran (SA)

(72) Inventors: Anas Almarzooq, AlRawda (SA); Charles Bradford, Wesley Chapel, FL (US); Mustafa Abdulmohsin, AlJesh (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/903,462

(22) Filed: Jun. 17, 2020

(51) Int. Cl.
| | |
|---|---|
| E21B 49/00 | (2006.01) |
| E21B 44/00 | (2006.01) |
| E21B 49/02 | (2006.01) |
| E21B 45/00 | (2006.01) |
| G01N 33/24 | (2006.01) |
| E21B 25/00 | (2006.01) |

(52) U.S. Cl.
CPC ............ *E21B 49/003* (2013.01); *E21B 44/00* (2013.01); *E21B 45/00* (2013.01); *E21B 49/02* (2013.01); *E21B 25/00* (2013.01); *G01N 33/24* (2013.01)

(58) Field of Classification Search
CPC .......... E21B 45/00; E21B 44/00; E21B 49/00; E21B 49/003; E21B 49/02
See application file for complete search history.

(56) References Cited

U.S. PATENT DOCUMENTS

| | | |
|---|---|---|
| 6,295,504 B1 | 9/2001 | Ye et al. |
| 7,032,689 B2 | 4/2006 | Goldman et al. |
| 8,977,523 B2 | 3/2015 | Ertas et al. |
| 9,249,654 B2 | 2/2016 | Strachan et al. |
| 9,970,266 B2 | 5/2018 | Marx et al. |
| 10,344,533 B2 | 7/2019 | Dashevsky et al. |
| 2006/0076161 A1 | 4/2006 | Weaver et al. |
| 2019/0345809 A1 | 11/2019 | Jain et al. |
| 2020/0040719 A1 | 2/2020 | Maniar et al. |
| 2020/0056478 A1* | 2/2020 | Lima ................ E21B 41/00 |

FOREIGN PATENT DOCUMENTS

| | | |
|---|---|---|
| WO | 2014066981 A1 | 5/2014 |
| WO | 2020018085 A1 | 1/2020 |

OTHER PUBLICATIONS

Hankins, David et al.; "An Integrated Approach for Drilling Optimization Using Advanced Drilling Optimizer" Journal of Petroleum Engineering, vol. 2015, Article ID 281276; pp. 1-12.
(Continued)

*Primary Examiner* — Kristyn A Hall
(74) *Attorney, Agent, or Firm* — Bracewell LLP; Constance G. Rhebergen; Christopher L. Drymalla

(57) ABSTRACT

Provided are techniques for drilling hydrocarbon wells based on evaluation of penetrated formation rock that include obtaining historical drilling data for one or more wells, determining a rock type mapping based on the historical drilling data, obtaining current drilling data for a well, determining, based on the current drilling data, a current rock identification (or "ROCKID"), and determining, based on the rock type mapping and the current rock identification, a rock type encountered by a drill bit drilling the well, where drilling parameters can be adjusted based on the rock type.

27 Claims, 5 Drawing Sheets

(56) References Cited

OTHER PUBLICATIONS

Hareland, G. et al.; "Increased Drilling Efficiency of Gas-Storage Wells Proven Using Drilling Simulator" SPE 114798, CIP C/SPE Gas Technology Symposium 2008, Calgary, Jun. 16-19, 2008; pp. 1-7.

Klyuchnikov, Nikita et al.; "Data-driven model for the identification of the rock type at a drilling bit" arXiv:1806.03218v3 [cs.LG] Mar. 25, 2019; pp. 1-24.

* cited by examiner

REAL-TIME WELL DRILLING EVALUATION SYSTEMS AND METHODS

FIELD

Embodiments relate generally to developing hydrocarbon wells, and more particularly to conducting well drilling operations based on evaluation of penetrated formation rock.

BACKGROUND

A well typically includes a wellbore (or a "borehole") that is drilled into the earth to provide access to a geologic formation that resides below the earth's surface (or a "subsurface formation"). A well may facilitate the extraction of natural resources (such as hydrocarbons and water) from a subsurface formation, facilitate the injection of substances into the subsurface formation, or facilitate the evaluation and monitoring of the subsurface formation. In the petroleum industry, hydrocarbon wells are often drilled to extract (or "produce") hydrocarbons, such as oil and gas, from subsurface formations.

Developing a hydrocarbon well for production typically involves a drilling stage, a completion stage, and a production stage. The drilling stage involves drilling a wellbore into a portion of the formation that is expected to contain hydrocarbons (often referred to as a "hydrocarbon reservoir" or a "reservoir"). The drilling process is often facilitated by a drilling rig that facilitates a variety of drilling operations, such as operating a cutting-type drill bit to cut (or "bore") the wellbore and operating a coring-type drill bit to cut and extract rock samples (or "cores") from the formation. The completion stage involves operations for making the well ready to produce hydrocarbons, such as installing casing, installing production tubing, installing valves for regulating production flow, or pumping substances into the well to fracture, clean or otherwise prepare the well and reservoir to produce hydrocarbons. The production stage involves producing hydrocarbons from the reservoir by way of the well. During the production stage, the drilling rig is normally replaced with a production tree that includes valves that are operable to regulate production flow. The production tree typically includes an outlet that is connected to a distribution network of midstream facilities, such as tanks, pipelines or transport vehicles that transport production from the well to downstream facilities, such as refineries or export terminals.

The various stages of developing a hydrocarbon well can include a variety of challenges that are addressed to successfully develop the well. For example, during drilling operations, a driller may periodically suspend or modify drilling operations based on an assessment of the drilling operation. For example, if a rate of penetration (ROP) of a drill bit decreases significantly, an operator may pull the drill string out of the wellbore to inspect the drill bit for wear. As a further example, if the drill bit is believed to be moving into a depth interval of interest within the formation, the operator may shift from a boring type drilling operation to a coring type drilling operation to extract a core from the interval.

SUMMARY

Drilling operations can be critical to effectively and efficiently developing hydrocarbon wells. For example, if a drill bit is worn or experiencing other issues, it can lead to a slow and inefficient drilling operation that can increase the time and cost of drilling the well. As a further example, if it is desirable to extract a rock sample (or "core") from a specific portion of the formation, and drilling into the location is not anticipated or identified, the drilling operation may cut through the portion of the formation before the sample can be acquired.

Unfortunately, it can be difficult to identify wear on a drill bit and the type of rock being penetrated by a drill bit. As a result, it can be difficult to determine when to pull the bit for inspection or when to conduct coring operations. For example, when using existing techniques that rely on direct monitoring rate of penetration (ROP) and other drilling conditions to identify drilling issues, if drilling hits a section of hard rock that decreases the drill bit rate of penetration (ROP), an operator may suspect the drill bit is worn and, in response, conduct an expensive and time consuming pull out of hole (POOH) operation, only to find that the drill bit is in good condition and the POOH operation was not necessary. As a further example, when using existing techniques that rely on assessment of drill cuttings to determine a type of rock currently engaged by the drill bit for the purpose of coring, given the delay of returning cutting to the surface, a driller may not know that the bit has penetrated into a new rock layer until after the bit has penetrated past the top of the layer. At that point, it may be too late to conduct a coring operation at the top of the layer.

Provided are systems and method for drilling hydrocarbon wells based on evaluation of penetrated formation rock. In some embodiments, drilling hydrocarbon wells based on evaluation of penetrated formation rock includes the following operations: (1) obtaining historical drilling data for one or more wells; (2) determining a rock type mapping based on the historical drilling data; (3) obtaining current drilling data for a well; (4) determining, based on the current drilling data, a current rock identification (or "ROCKID"); and (5) determining, based on the rock type mapping and the current rock identification, a rock type currently encountered by a drill bit drilling the well.

In some instances, a rock type may be determined based on drilling data that is available in real-time, which can in turn enable a well operator to determine a rock type currently being engaged by a drill bit and conduct corresponding drilling operation decisions in real-time (e.g., within five minutes of a drill bit engaging the rock identified). For example, in comparison to a technique that relies on assessment of drill cutting to determine a type of rock engage by the drill bit (which is delayed by at least the amount of time that is required for the drill cuttings to travel from the drill bit to the surface and the time to assess the cuttings), a type of rock engage by the drill bit may be determined almost instantaneously, in the relatively short amount of time that is required to collect and process the operational drilling parameters, such as rate of penetration (ROP), weight-on-bit (WOB), rotational speed of the drill string (RPM), drilling fluid flowrate, and surface gas concentration(s) (C), which are often readily available without significant delay.

In some embodiments, drilling operation parameters are determined based on a rock type encountered, and a drilling operation can be conducted/adjusted based on the determined drilling operation parameters. For example, a well operator may decide to adjust one or more drilling parameters of an ongoing drilling operation of the well (e.g., decide to slow a rotational speed of the drill string) based on a determined rock type encountered, and, in turn, control operation of a drilling system in accordance with the adjusted parameters (e.g., control a drive system to operate at a slower rotational speed). As a further example, a well operator may decide to transition to a different phase or type of drilling operation (e.g., decide to inspect the drill bit or decide to transition to a coring operation) based on a determined rock type encountered, and, in turn, control operation of a drilling system in accordance with the transition (e.g., control the drilling system to conduct a POOH operation to inspect the drill bit, or control the drilling system to conduct a POOH operation to change over to a coring-type drill bit and return the drill string into the wellbore to conduct a coring-type drilling operation).

Provided in some embodiments is a hydrocarbon well drilling system that includes the following: a well drilling system adapted to drill a wellbore of a hydrocarbon well into a subsurface formation, the well drilling system including: a drill string including: a drill bit; drill pipe; and drilling sensors adapted to sense characteristics of a drilling operation conducted by the well drilling system; a well control system adapted to perform the following operations: obtaining, by way of the drilling sensors, drilling data that is indicative of characteristics of the drilling operation, the drilling data including: rate of penetration data that is indicative of rate of penetration of the drill bit into the subsurface formation; weight on bit data that is indicative of weight acting on the drill bit; rotation data that is indicative of rotational speed of the drill pipe; torque data that is indicative of a torque acting on the drill pipe; fluid circulation data that is indicative of rate of drilling fluid circulation; surface gas data that is indicative of concentrations of one or more surface gases produced; determining, based on the drilling data, the following drilling characteristics for a given point in time: an observed rate of penetration of the drill bit at the given point in time ($ROP_i$) determined based on the rate of penetration data, a product of observed concentrations of one or more surface gases produced at the given point in time ($C_{prod_i}$) determined based on the surface gas data; a sum of observed concentrations of one or more surface gases produced at the given point in time ($C_{sum_i}$) determined based on the surface gas data; an observed weight acting on the drill bit at the given point in time ($WOB_i$ determined based on the weight on bit data; an observed torque acting on the drill pipe at the given point in time ($T_i$) is determined based on the torque data; an observed rotational speed of the drill pipe at the given point in time ($RPM_i$) determined based on the rotation data; and an observed rate of drilling fluid circulation at the given point in time ($FLWPMPS_i$) determined based on the fluid circulation data; applying the drilling data to the following rock identification relationship to determine a rock identification value ($ROCKID_i$) that is indicative of a type of rock engaged by the drill bit at the given point in time:

$$ROCKID_i = \frac{B * \left(\log_{10}\left(\frac{ROP_i}{ROPB_i}\right)\right) * C_{prod_i}}{(C_{sum_i} * A)} * \frac{WOB_i * T_i * RPM_i * FLWPMPS_i}{DCF}$$

where: $ROPB_i$ is a base rate of penetration of the drill bit, DCF is a drilling calibration factor, and A and B are calibration constants associated with the subsurface formation; determining, based on the $ROCKID_i$, a type of rock engaged by the drill bit at the given point in time; determining, based on the type of rock determined, a drilling operation parameter; and conducting a drilling operation in accordance with the drilling operation parameter.

In some embodiments, the operations further include: determining a rock type mapping that maps ROCKID values to associated types of rocks, where the rock type mapping maps the $ROCKID_i$ to the type of rock, and the type of rock engaged by the drill bit at the given point in time is determined based the mapping of the $ROCKID_i$ to the type of rock. In certain embodiments, determining a rock type mapping includes: identifying drilling parameters associated with known rock types; applying the drilling parameters associated with known rock types to the rock identification relationship to generate ROCKID values; associating, based on the ROCKID values generated and the associated known rock types, groups of ROCKID values with respective ones of the known rock types. In some embodiments, the operations further include determining the drilling calibration factor (DCF) based on a comparison of determined ROCKID values for one or more points in time to known types of rocks encountered during drilling at the one or more points in time. In certain embodiments, the known types of rocks encountered during drilling at the one or more points in time are determined based on inspection of formation rock encountered by the drill bit at the one or more points in time. In some embodiments, the inspection includes physical inspection of one or more samples of rock extracted from the location of the drill bit at the one or more points in time. In certain embodiments, the inspection includes inspection of well logs of a depth interval that includes the location of the drill bit at the one or more points in time. In some embodiments, the drilling operation parameter includes a time to conduct a pull out of hole operation to inspect the drill bit, and conducting a drilling operation in accordance with the drilling operation parameter includes conducting the pull out of hole operation to inspect the drill bit. In certain embodiments, the drilling operation parameter includes a time to conduct a coring operation, and conducting a drilling operation in accordance with the drilling operation parameter includes conducting the coring operation.

Provided in some embodiments is a method of drilling a hydrocarbon well that includes the following: obtaining, by way of the drilling sensors, drilling data that is indicative of characteristics of drilling a wellbore of a hydrocarbon well into a subsurface formation by way of a drilling system that includes a drill string that includes a drill bit, drill pipe and the drilling sensors, the drilling data including: rate of penetration data that is indicative of rate of penetration of the drill bit into the subsurface formation; weight on bit data that is indicative of weight acting on the drill bit; rotation data that is indicative of rotational speed of the drill pipe; torque data that is indicative of a torque acting on the drill pipe; fluid circulation data that is indicative of rate of drilling fluid circulation; surface gas data that is indicative of concentrations of one or more surface gases produced; determining, based on the drilling data, the following drilling characteristics for a given point in time: an observed rate of penetration of the drill bit at the given point in time ($ROP_i$) determined based on the rate of penetration data; a product of observed concentrations of one or more surface gases produced at the given point in time ($C_{prod_i}$) determined based on the surface gas data; a sum of observed concentrations of one or more surface gases produced at the given point in time ($C_{sum_i}$) determined based on the surface gas data; an observed weight acting on the drill bit at the given point in time ($WOB_i$) determined based on the weight on bit data; an observed torque acting on the drill pipe at the given point in time ($T_i$) is determined based on the torque data; an observed rotational speed of the drill pipe at the given point in time ($RPM_i$) determined based on the rotation data; and an observed rate of drilling fluid circulation at the given point in time ($FLWPMPS_i$) determined based on the fluid circulation data; applying the drilling data to the following rock identification relationship to determine a rock identification value (ROCKID$_i$) that is indicative of a type of rock engaged by the drill bit at the given point in time:

$$ROCKID_i = \frac{B*\left(\log_{10}\left(\frac{ROP_i}{ROPB_i}\right)\right)*C_{prod_i}}{(C_{sum_i}*A)} * \frac{WOB_i*T_i*RPM_i*FLWPMPS_i}{DCF}$$

where: ROPB$_i$ is a base rate of penetration of the drill bit, DCF is a drilling calibration factor, and A and B are calibration constants associated with the subsurface formation; determining, based on the ROCKID$_i$, a type of rock engaged by the drill bit at the given point in time; determining, based on the type of rock determined, a drilling operation parameter; and conducting a drilling operation in accordance with the drilling operation parameter.

In some embodiments, the method further includes: determining a rock type mapping that maps ROCKID values to associated types of rocks, where the rock type mapping maps the ROCKID$_i$ to the type of rock, and the type of rock engaged by the drill bit at the given point in time is determined based the mapping of the ROCKID$_i$ to the type of rock. In certain embodiments, determining a rock type mapping includes: identifying drilling parameters associated with known rock types; applying the drilling parameters associated with known rock types to the rock identification relationship to generate ROCKID values; associating, based on the ROCKID values generated and the associated known rock types, groups of ROCKID values with respective ones of the known rock types. In some embodiments, the method further includes determining the drilling calibration factor (DCF) based on a comparison of determined ROCKID values for one or more points in time to known types of rocks encountered during drilling at the one or more points in time. In certain embodiments, the known types of rocks encountered during drilling at the one or more points in time are determined based on inspection of formation rock encountered by the drill bit at the one or more points in time. In some embodiments, the inspection includes physical inspection of one or more samples of rock extracted from the location of the drill bit at the one or more points in time. In certain embodiments, the inspection includes inspection of well logs of a depth interval that includes the location of the drill bit at the one or more points in time. In some embodiments, the drilling operation parameter includes a time to conduct a pull out of hole operation to inspect the drill bit, and conducting a drilling operation in accordance with the drilling operation parameter includes conducting the pull out of hole operation to inspect the drill bit. In certain embodiments, the drilling operation parameter includes a time to conduct a coring operation, and conducting a drilling operation in accordance with the drilling operation parameter includes conducting the coring operation.

Provided in some embodiments is non-transitory computer readable storage medium having program instructions stored thereon that are executable by a computer processor to perform the following operations for drilling a hydrocarbon well: obtaining, by way of drilling sensors, drilling data that is indicative of characteristics of drilling a wellbore of a hydrocarbon well into a subsurface formation by way of a drilling system that includes a drill string that includes a drill bit, drill pipe and the drilling sensors, the drilling data including: rate of penetration data that is indicative of rate of penetration of the drill bit into the subsurface formation; weight on bit data that is indicative of weight acting on the drill bit; rotation data that is indicative of rotational speed of the drill pipe; torque data that is indicative of a torque acting on the drill pipe; fluid circulation data that is indicative of rate of drilling fluid circulation; surface gas data that is indicative of concentrations of one or more surface gases produced; determining, based on the drilling data, the following drilling characteristics for a given point in time: an observed rate of penetration of the drill bit at the given point in time (ROP$_i$) determined based on the rate of penetration data, a product of observed concentrations of one or more surface gases produced at the given point in time ($C_{prod_i}$) determined based on the surface gas data; a sum of observed concentrations of one or more surface gases produced at the given point in time ($C_{sum_i}$) determined based on the surface gas data; an observed weight acting on the drill bit at the given point in time (WOB$_i$) determined based on the weight on bit data; an observed torque acting on the drill pipe at the given point in time (T$_i$) is determined based on the torque data; an observed rotational speed of the drill pipe at the given point in time (RPM$_i$) determined based on the rotation data; and an observed rate of drilling fluid circulation at the given point in time (FLWPMPS$_i$) determined based on the fluid circulation data; applying the drilling data to the following rock identification relationship to determine a rock identification value (ROCKID$_i$) that is indicative of a type of rock engaged by the drill bit at the given point in time:

$$ROCKID_i = \frac{B*\left(\log_{10}\left(\frac{ROP_i}{ROPB_i}\right)\right)*C_{prod_i}}{(C_{sum_i}*A)} * \frac{WOB_i*T_i*RPM_i*FLWPMPS_i}{DCF}$$

where: ROPB$_i$ is a base rate of penetration of the drill bit, DCF is a drilling calibration factor, and A and B are calibration constants associated with the subsurface formation; determining, based on the ROCKID$_i$, a type of rock engaged by the drill bit at the given point in time; determining, based on the type of rock determined, a drilling operation parameter; and conducting a drilling operation in accordance with the drilling operation parameter. In some embodiments, the operations further include: determining a rock type mapping that maps ROCKID values to associated types of rocks, where the rock type mapping maps the ROCKID$_i$ to the type of rock, and the type of rock engaged by the drill bit at the given point in time is determined based the mapping of the ROCKID$_i$ to the type of rock. In certain embodiments, determining a rock type mapping includes: identifying drilling parameters associated with known rock types; applying the drilling parameters associated with known rock types to the rock identification relationship to generate ROCKID values; and associating, based on the ROCKID values generated and the associated known rock types, groups of ROCKID values with respective ones of the known rock types. In some embodiments, the operations further including determining the drilling calibration factor (DCF) based on a comparison of determined ROCKID values for one or more points in time to known types of rocks encountered during drilling at the one or more points in time. In certain embodiments, the known types of rocks encountered during drilling at the one or more points in time are determined based on inspection of formation rock encountered by the drill bit at the one or more points in time. In certain embodiments, the inspection includes physical inspection of one or more samples of rock extracted from the location of the drill bit at the one or more points in time. In some embodiments, the inspection includes inspection of well logs of a depth interval that includes the location of the drill bit at the one or more points in time. In certain embodiments, the drilling operation parameter includes a time to conduct a pull out of hole operation to inspect the drill bit, and conducting a drilling operation in accordance with the drilling operation parameter includes conducting the pull out of hole operation to inspect the drill bit. In some embodiments, the drilling operation parameter includes a time to conduct a coring operation, and conducting a drilling operation in accordance with the drilling operation parameter includes conducting the coring operation.

Figure 1:
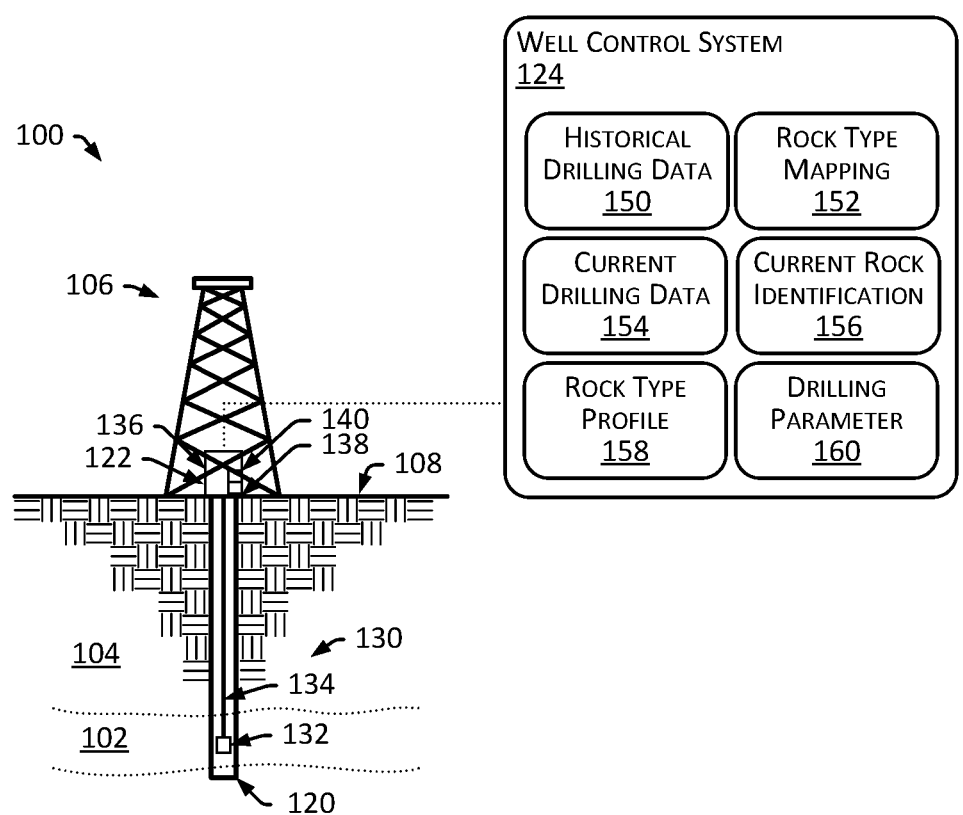
FIG. 1 is diagram that illustrates a well environment in accordance with one or more embodiments.

While this disclosure is susceptible to various modifications and alternative forms, specific embodiments are shown by way of example in the drawings and will be described in detail. The drawings may not be to scale. It should be understood that the drawings and the detailed descriptions are not intended to limit the disclosure to the particular form disclosed, but are intended to disclose modifications, equivalents, and alternatives falling within the scope of the present disclosure as defined by the claims.

DETAILED DESCRIPTION

Described are embodiments of novel systems and method for drilling hydrocarbon wells based on evaluation of penetrated formation rock. In some embodiments, drilling hydrocarbon wells based on evaluation of penetrated formation rock includes the following operations: (1) obtaining historical drilling data for one or more wells; (2) determining a rock type mapping based on the historical drilling data; (3) obtaining current drilling data for a well; (4) determining, based on the current drilling data, a current rock identification (or "ROCKID"); and (5) determining, based on the rock type mapping and the current rock identification, a rock type currently encountered by a drill bit drilling the well.

In some instances, a rock type may be determined based on drilling data that is available in real-time, which can in turn enable a well operator to determine a rock type currently being engaged by a drill bit and conduct corresponding drilling operation decisions in real-time (e.g., within five minutes of a drill bit engaging the rock identified). For example, in comparison to a technique that relies on assessment of drill cutting to determine a type of rock engage by the drill bit (which is delayed by at least the amount of time that is required for the drill cuttings to travel from the drill bit to the surface and the time to assess the cuttings), a type of rock engage by the drill bit may be determined almost instantaneously, in the relatively short amount of time that is required to collect and process the operational drilling parameters, such as rate of penetration (ROP), weight-on-bit (WOB), rotational speed of the drill string (RPM), drilling fluid flowrate, and surface gas concentration(s) (C), which are often readily available without significant delay.

In some embodiments, drilling operation parameters are determined based on a rock type encountered, and a drilling operation can be conducted/adjusted based on the determined drilling operation parameters. For example, a well operator may decide to adjust one or more drilling parameters of an ongoing drilling operation of the well (e.g., decide to slow a rotational speed of the drill string) based on a determined rock type encountered, and, in turn, control operation of a drilling system in accordance with the adjusted parameters (e.g., control a drive system to operate at a slower rotational speed). As a further example, a well operator may decide to transition to a different phase or type of drilling operation (e.g., decide to inspect the drill bit or decide to transition to a coring operation) based on a determined rock type encountered, and, in turn, control operation of a drilling system in accordance with the transition (e.g., control the drilling system to conduct a POOH operation to inspect the drill bit, or control the drilling system to conduct a POOH operation to change over to a coring-type drill bit and return the drill string into the wellbore to conduct a coring-type drilling operation).

FIG. 1 is a diagram that illustrates a well environment 100 in accordance with one or more embodiments. In the illustrated embodiment, the well environment 100 includes a reservoir ("reservoir") 102 located in a subsurface formation ("formation") 104 and a well system ("well") 106.

The formation 104 may include a porous or fractured rock formation that resides beneath the earth's surface (or "surface") 108. The reservoir 102 may be a hydrocarbon reservoir defined by a portion of the formation 104 that contains (or that is at least determined or expected to contain) a subsurface pool of hydrocarbons, such as oil and gas. The formation 104 and the reservoir 102 may each include layers of rock having varying characteristics, such as varying degrees of permeability, porosity, and fluid saturation. In the case of the well 106 being operated as a production well, the well 106 may be a hydrocarbon production well that is operable to facilitate the extraction of hydrocarbons (or "production") from the reservoir 102. In the case of the well 106 being operated as an injection well, the well 106 may be a hydrocarbon injection well that is operable to facilitate the injection of substances (e.g., water or gas) into the reservoir 102.

The well 106 may include a wellbore 120, a drilling system 122, and a well control system ("control system") 124. The wellbore 120 may be, for example, a bored hole that extends from the surface 108 into a target zone of the formation 104, such as the reservoir 102. The wellbore 120 may be created, for example, by a cutting-type drill bit of the drilling system 122 boring through the formation 104 and the reservoir 102. An upper end of the wellbore 120 (e.g., located at or near the surface 108) may be referred to as the "up-hole" end of the wellbore 120. A lower end of the wellbore 120 (e.g., terminating in the formation 104) may be referred to as the "down-hole" end of the wellbore 120.

In some embodiments, the drilling system 122 includes drilling devices that facilitate creation of the wellbore 120. For example, the drilling system 122 may include a drill string 130 that includes a drill bit 132 and drill pipe 134. The drill bit 132 may be attached to a lower (or "down-hole") end of the drilling pipe 134. During a boring-type drilling operation, the drill bit 132 may be a cutting-type drill bit having cutting teeth, and the dill pipe 134 may be rotated to impart a rotation of the drill bit 132 and its cutting teeth to facilitate the drill bit 132 boring though the formation 104 to create the wellbore 120. During a coring-type drilling operation, the drill bit 132 may be a coring-type drill bit designed to cut a cylindrical shaped rock sample (or "core"), and the dill pipe 134 may be rotated to impart a rotation of the drill bit 132 to facilitate the drill bit 132 cutting a core from the formation 104, the drill pipe 134 and the drill bit 132 (with the core) may be retrieved to the surface 108. The retrieved (or "extracted") core may be physically inspected, for example, in a laboratory. The torque to rotate the dill pipe 134 may be provided by a drive system 136, such as a kelly drive system or a top drive system. Drilling fluid may be circulated to facilitate drilling operations. For example, drilling fluid (e.g., drilling mud) may be pumped down the drill pipe 134, where it is expelled through the drill bit 132 and subsequently routed up an annulus of the wellbore 120. The circulated fluid may, for example, provide cooling and lubrication of the drill bit 132, flush drill cuttings from the wellbore 120, and counteract fluid pressures in the wellbore 120. Circulation of the drilling fluid may be facilitated by drilling fluid pumps 138 that are operable pump the drilling fluid down the drill pipe 134.

In some embodiments, the drilling system 122 includes drilling sensors 140 that are operable to monitor various aspects of drilling operations. The drilling sensors 140 may include a depth sensor that is operable to sense a depth of the drill bit 132 and generate corresponding depth data. The depth data may include, for example, a set of time series measurements that are indicative of depths of the well bit 132 at respective instances of time across a time interval. Such depth data may, for example, be used to determine a rate of penetration of the drill bit 132 into the subsurface formation 104 (or a "rate of penetration" or "ROP").

The drilling sensors 140 may include a weight-on-bit (WOB) sensor that is operable to sense a downward force exerted on the drill bit 132 and generate corresponding WOB data. The WOB data may include, for example, a set of time series measurements that are indicative of downward force exerted on the drill bit 132 at respective instances of time across the time interval. In some instances, the WOB may be determined based on a weight of components of the drill string 130 acting on the drill bit 132.

The drilling sensors 140 may include a rotational speed sensor that is operable to sense a rotational speed of the drill string 130 and generate corresponding rotational speed data. The rotational speed data may include, for example, a set of time series measurements that are indicative of rotational speed of the drill pipe 134 at respective instances of time across the time interval.

The drilling sensors 140 may include a drilling fluid flowrate sensor that is operable to sense a flowrate of drilling fluid circulated in the wellbore 120 and generate corresponding drilling fluid flowrate data. The drilling fluid flowrate data may include, for example, a set of time series measurements that are indicative of flowrate of drilling fluid being pumped into (or exiting from) the wellbore 120 at respective instances of time across the time interval. In some instances, the flowrate of drilling fluid may be determined based on operational parameters of pumps that are circulating the drilling fluid.

The drilling sensors 140 may include a surface gas sensor that is operable to sense gases produced from the wellbore 120 and generate corresponding surface gas data. The surface gas data may include, for example, a set of time series measurements that are indicative of concentrations of one or more gases in drilling fluid exiting the wellbore 120 (or "surface gases") at respective instances of time across the time interval.

In some embodiments, the well control system 124 is operable to control various operations of the well 106, such as well drilling operations, well completion operations, and well production operations. For example, the well control system 124 may include a well system memory and a well system processor that are capable of performing the various processing and control operations of the well control system 124 described here. In some embodiments, the well control system 124 includes a computer system that is the same as or similar to that of computer system 1000 described with regard to at least FIG. 5.

In some embodiments, the well control system 124 is operable to identify and implement well drilling operations based on observed drilling parameters. This may include, for example, the well control system 124 performing the following operations: (1) obtaining historical drilling data 150 for the well 106 (or other wells); (2) determining a rock type mapping 152 based on the historical drilling data 150; (3) obtaining current drilling data 154 for the well 106; (4) determining, based on the current drilling data 154, a current rock identification (or "ROCKID") 156; and (5) determining, based on the current rock identification and the rock type mapping 152, a rock type encountered.

In some instances, a rock type may be determined based on drilling data that is available in real-time, which can in turn enable a well operator to determine a rock type currently being engaged by a drill bit and conduct corresponding drilling operation decisions in real-time (e.g., within five minutes of a drill bit engaging the rock identified). For example, in comparison to a technique that relies on assessment of drill cutting to determine a type of rock engage by the drill bit (which is delayed by at least the amount of time that is required for the drill cuttings to travel from the drill bit to the surface and the time to assess the cuttings), a type of rock engage by the drill bit may be determined almost instantaneously, in the relatively short amount of time that is required to collect and process the operational drilling parameters, such as rate of penetration (ROP), weight-on-bit (WOB), rotational speed of the drill string (RPM), drilling fluid flowrate, and surface gas concentration(s) (C), which are often readily available without an significant delay.

In some embodiments, the well control system 124 (or another well operator) may determining drilling operation parameters 160 based on the rock type encountered, and conduct a drilling operation based on the determined drilling operation parameters 160. For example, the well control system 124 (or another well operator) may decide to adjust one or more drilling parameters 160 of an ongoing drilling operation of well 106 (e.g., decide to slow a rotational speed of the drill string 130), and, in turn, control operation of the drilling system 122 in accordance with the adjusted parameters (e.g., control the drive system 136 to operate at a slower rotational speed). As a further example, the well control system 124 (or another well operator) may decide to transition to a different phase or type of drilling operation (e.g., decide to inspect the drill bit or decide to transition to a coring operation), and, in turn, control operation of the drilling system 122 in accordance with the transition (e.g., control the drilling system 122 to conduct a POOH operation to inspect the drill bit 132, or control the drilling system 122 to conduct a POOH operation to change over to a coring-type drill bit 132 and return the drill string 130 into the wellbore 120 to conduct a coring-type drilling operation). A coring operation may be conducted, for example, in response to determining that the drill bit 132 is encountering a change in the type of rock penetrated, which can signal the bottom/end of a current layer of rock penetrated by the drill bit 132 or the top/start of a next layer of rock to be penetrated by the drill bit 132. In some embodiments, a rock type profile 158 indicative of the rock types versus depth in the wellbore 120 (or the formation 104) is generated (see, e.g., FIG. 4).

Figure 2:
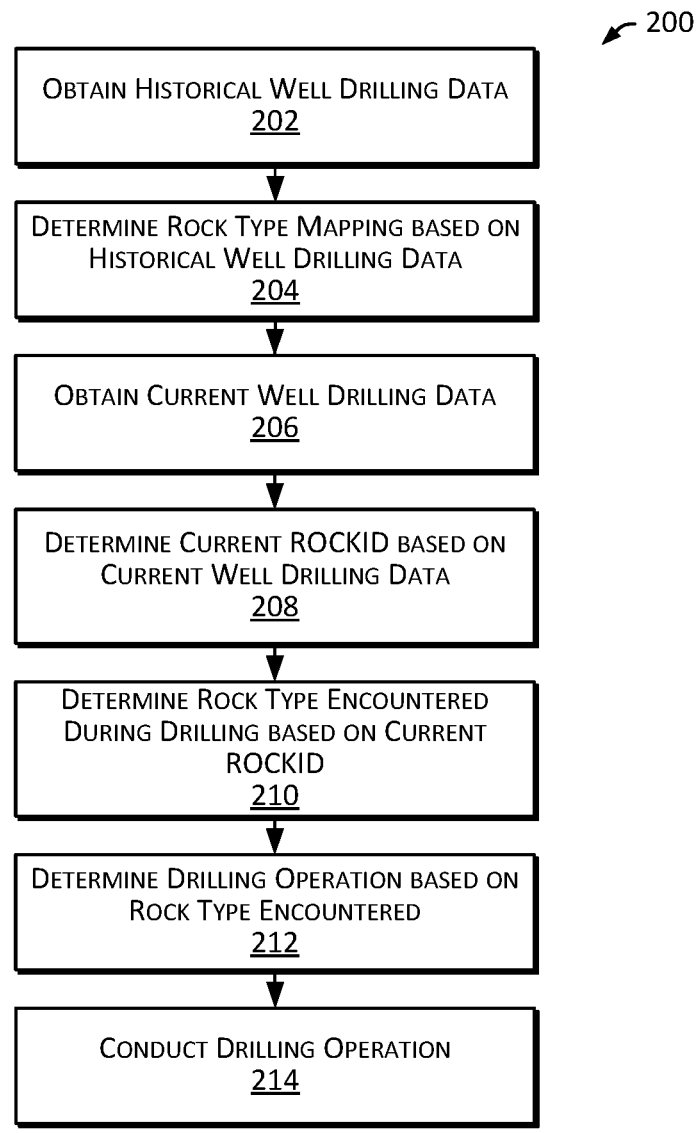
FIG. 2 is a flowchart that illustrates a method of drilling a well in accordance with one or more embodiments.

FIG. 2 is a flowchart that illustrates a method 200 of drilling hydrocarbon well in accordance with one or more embodiments. In the context of the well 106, some or all of the operations of method 200 may be performed by the well control system 124 (or another operator of the well 106).

In some embodiments, method 200 includes obtaining historical well drilling data (block 202). This may include obtaining historical well drilling data that is indicative of observed characteristics of the drilling operation of one or more hydrocarbon wells. For example, obtaining historical well drilling data may include the well control system 124 (or another operator of the well 106) obtaining well drilling data that is indicative of observed characteristics of the drilling of the well 106, or of other similarly situated wells (such as other wells in the formation 104), to date. For example, the historical drilling data 150 for the well 106 may include historical measurements of operational drilling parameters, such as rate of penetration (ROP) (e.g., in feet per hour (ft/hr)) of the drill bit 132, weight-on-bit (WOB) (e.g., in pounds force (lbf)), rotational speed of the drill string 130 (e.g., in revolutions per minute (rpm)), torque acting on the drill pipe (T) (e.g., in pound-foot (lbf*ft)) flowrate of drilling fluid circulating in the wellbore 120 (e.g., in cubic feet per second (cfs)), and surface gas concentration(s) (C) (e.g., in ppm) collected over the course of drilling of the well 106 by way of respective ones of the drilling sensors 140 (or collected over the course of drilling of one or more other wells).

In some embodiments, method 200 includes determining a rock type mapping based on the historical drilling data (block 204). This may include (1) determining, for sets of historical drilling data for respective points in time, corresponding rock type information that includes (a) a type of rock associated with the set of historical drilling data, and (b) a corresponding rock identification value (or "ROCKID"), and (2) determining, based on the rock type information, a mapping of rock identification values (or "ROCKID") to types of rock. For example, determining a rock type mapping based on the historical drilling data may include the well control system 124 (or another operator of the well 106) (1) determining, for sets of historical drilling data for respective points in time within a time interval of 12:00 am Jan. 1, 2020 to 1:00 pm Jan. 15, 2020, corresponding rock type information that includes (a) type of rock associated with the set of historical drilling data, and (b) a corresponding rock identification value (or "ROCKID") (e.g., a first rock type and a first ROCKID for 12:00 am Jan. 1, 2020, a second rock type and a second ROCKID for 12:01 am Jan. 1, 2020, a third rock type and a third ROCKID for 12:02 am Jan. 1, 2020, and so forth), and (2) determining, based on the rock type information, a mapping of rock identification (or "ROCKIDs") values to types of rock (e.g., mapping ROCKIDs in a first range with a first type of rock, ROCKIDs in a second range with a second type of rock, ROCKIDs in a third range with a third type of rock, and so forth).

Figure 3:
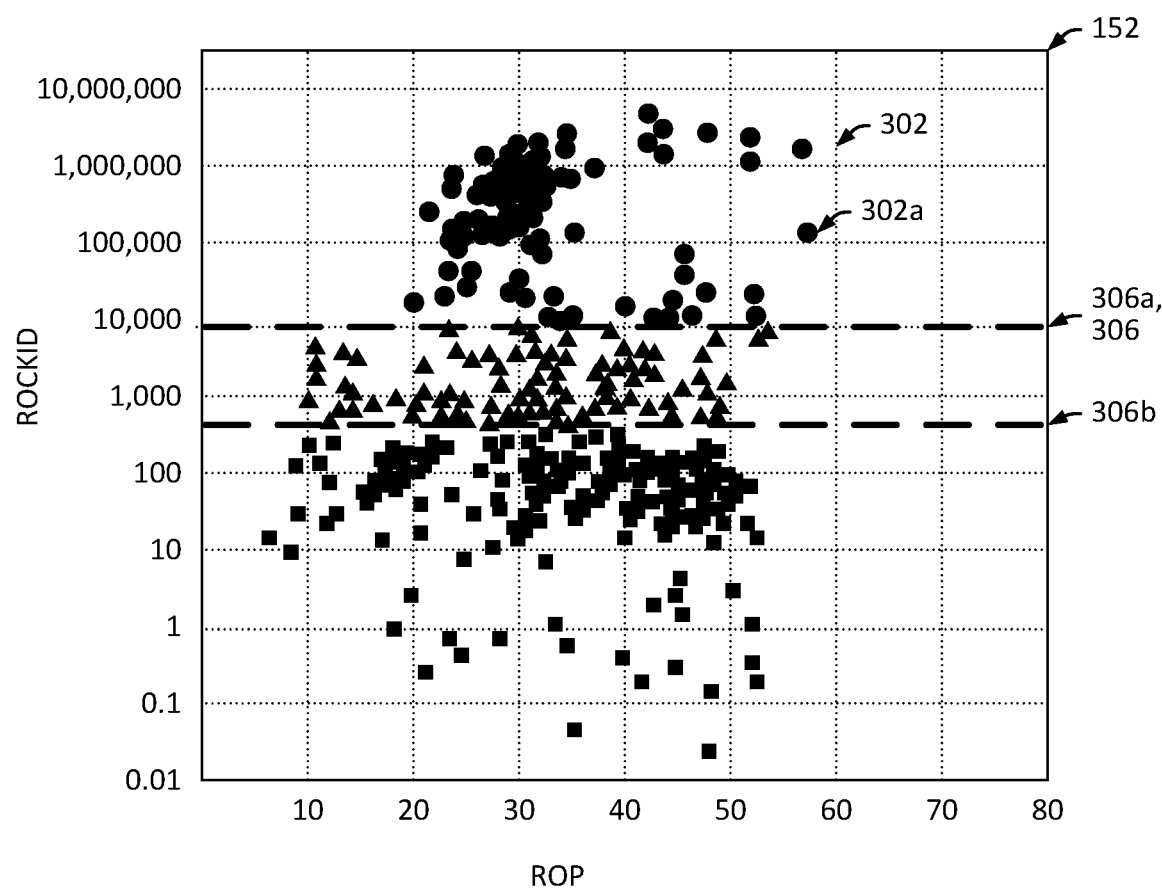
FIG. 3 is a diagram that illustrates a rock type mapping in accordance with one or more embodiments.

FIG. 3 is a diagram that illustrates a rock type mapping 152 in accordance with one or more embodiments. The rock type mapping 152 depicts individual ROCKID data points 302, and groupings of the data points 302 into different rock types, as indicated by boundaries 306. In the illustrated embodiments, each data point 302 is defined by a drilling parameter of interest (e.g., ROP) and a corresponding ROCKID value.

As described, in some embodiments, the ROCKID value for a given point in a drilling operation is determined based on application of a set of drilling parameters for that point in the drilling operation to a ROCKID algorithm to generate a corresponding ROCKID value for the set of drilling parameters and, thus, for that point in the drilling operation (see, e.g., Equation 1 described here). For example, the data point 302a may be defined by application of measured (or "observed") values of rate of penetration (ROP), weight-on-bit (WOB), rotational speed of the drill string (RPM), drilling fluid flowrate, and surface gas concentration(s) at 3:00 pm on Jan. 20, 2020, obtained by way of the drilling sensors 140.

In some embodiments, each of the data points 302 is associated with a respective rock type. For example, the data points 302 represented by circles, triangles and squares may be associated with a first rock type (rock type A), a second rock type (rock type B) and a third rock type (rock type C), respectively. In some embodiments, the rock type for a given data point (and its associated drilling conditions/parameters) is determined based on a verification of the rock at the location associated with the data point. For example, where the data point 302a is associated with a depth of about 1,000 feet in the wellbore 120 (e.g., the drill bit 132 is determined to be at a depth of about 1,000 feet at the time the corresponding set of drilling parameters used to generate the ROCKID value are acquired), the rock type A that is associated with the data point 302a may be determined based on an assessment of the rock located at the depth of about 1,000 feet in the wellbore 120. In some embodiments, the assessment may include a physical assessment of core samples. For example, the assessment may include a laboratory assessment of a core sample extracted from a depth of about 1,000 feet in the wellbore 120 to determine that the formation has rock type A at the depth of about 1,000 feet. In some embodiments, the assessment may include an assessment of one or more well logs. For example, the assessment may include assessment of well logs that span the depth of about 1,000 feet in the wellbore 120 to determine that the formation has rock type A at the depth of about 1,000 feet.

In some embodiments, different ranges of ROCKID values are associated with respective rock types. For example, ROCKID values above about 10,000 may be associated with rock type A (as indicated by boundary 306a), ROCKID values between about 800 and 10,000 may be associated with rock type B (as indicated by boundaries 306a and 306b), and ROCKID values below about 800 may be associated with rock type C (as indicated by boundary 306c). In some embodiments, the boundaries are determined based on groupings of ROCKID values associated with given rock types.

As noted above, in some embodiments, ROCKID values are determined based on application of respective sets of drilling parameters to a ROCKID algorithm. For example, a ROCKID value for a given point in time during a drilling operation may be determined based on application of a set of drilling parameters for the point in time to the following ROCKID algorithm to generate a corresponding ROCKID value for the point in time:

$$ROCKID_i = \frac{B * \left(\log_{10}\left(\frac{ROP_i}{ROPB_i}\right)\right) * C_{prod_i}}{(C_{sum_i} * A)} * \frac{WOB_i * T_i * RPM_i * FLWPMPS_i}{DCF}$$

where:

ROCKID$_i$ is an identifier of a type of rock engaged by the drill bit at the given point in time, ROP$_i$ is an observed rate of penetration of the drill bit at the given point in time (e.g., in units of feet per hour (ft/hr)), ROPB$_i$ is a base rate of penetration of the drill bit (e.g., in units of feet per hour (ft/hr)), $C_{prod_i}$ is a product of concentrations of one or more surface gases at the given point in time (e.g., in units of parts per million (ppm)), $C_{sum_i}$ is a sum of rates of production of concentration of one or more surface gases at the given point in time (e.g., in units of parts per million (ppm)), WOB$_i$ is an observed weight acting on the drill bit at the given point in time (e.g., in units of pounds force (lbf)), T$_i$ is an observed torque acting on the drill pipe at the given point in time (e.g., in units of pound-foot (lbf*ft)), RPM$_i$ is an observed rotational speed of the drill pipe at the given point in time (e.g., in units of revolutions per minute (rpm)), FLWPMPS$_i$ is an observed rate of drilling fluid circulation at the given point in time (e.g., in units of cubic feet per second (cfs)), DCF is a drilling calibration factor (e.g., unitless), and A and B are calibration constants associated with the formation in which the wellbore is being drilled (e.g., A or B may have unitless values in the range of about 0.01 to 100, such as A=1 and B=2).

In some embodiments, ROP$_i$, WOB$_i$, T$_i$, RPM$_i$, FLWPMPS$_i$, and $C_{prod_i}$ and $C_{sum_i}$ for a given point in timer are determined based on respective data points of rate of penetration data, weight on bit data, torque data, rotation data, fluid circulation data and surface gas data. For example, the historical drilling data 150 may include rate of penetration data defined by a set of time series data indicative of rate of penetration of the drill bit into the subsurface formation (ROP), weight on bit data defined by a set of time series data indicative of weight acting on the drill bit (WOB), rotation data defined by a set of time series data indicative of rotational speed of the drill pipe (RPM), torque data defined by a set of time series data indicative of a torque acting on the drill pipe (T), fluid circulation data defined by a set of time series data indicative of rate of drilling fluid circulation (FLWPMPS), and surface gas data comprising a set of time series data indicative of rates of production of one or more gases at the surface (C). In such an embodiment, the ROCKID for the data point 302a may be defined by application of respective values of the time series datasets for rate of penetration (ROP), weight-on-bit (WOB), rotational speed of the drill string (RPM), rate of drilling fluid circulation (FLWPMPS), and concentration(s) of one or more surface gases (C) at 3:00 pm on Jan. 20, 2020.

In some embodiments, the values applied to the relationship may be normalized. For example, one, some or all of the rate of penetration of the drill bit into the subsurface formation (ROP), the weight acting on the drill bit (WOB), the rotational speed of the drill pipe (RPM), the torque acting on the drill pipe (T), the rate of drilling fluid circulation (FLWPMPS), and the surface gas concentration(s) (C) may be normalized values of the respective parameter.

The base rate of penetration (ROPB$_i$) may enable the relationship of equation 1 to more accurately reflect deviations from expected drilling parameters. In some embodiments, the base rate of penetration (ROPB$_i$) is defined based on expected (or "normal") rate of penetration for the corresponding drilling operation. For example, where the rate of penetration at a depth of about 1,000-2,000 feet in the formation 104 is expected to be about two feet per hour (e.g., based on prior assessments of the rock of the formation 104 or similar formations), the ROPB$_i$ may be 2 ft/hr for ROCKID value determinations for drilling operations where the drill bit 132 is engaging rock in the range of about 1,000-2,000 feet in the formation 104, including the determination of the ROCKID$_i$ for the data point 302a. The ROPB$_i$ may, for example, be varied based on depth/location to account for variations in drilling conditions.

The drilling calibration factor (DCF) may provide for fine tuning of the relationship to generate ROCKID values that more accurately represent corresponding types of rock. In some embodiments, the drilling calibration factor (DCF) is determined based on a verification that includes a comparison of determined ROCKID values for one or more points in time to known types of rocks encountered during drilling at the one or more points in time. For example, the drilling calibration factor (DCF) may be determined by way of a history matching of ROCKID values for known types of rock (e.g., identified by way of assessments of cores or well logs) to historical categorizations of ROCKID values with types of rock.

In some embodiments, method 200 includes obtaining current well drilling data (block 206). This may include obtaining well drilling data that is indicative of observed characteristics of the drilling operation of a hydrocarbon well at a given point in time (and depth). For example, obtaining current well drilling data may include the well control system 124 (or another operator of the well 106) obtaining current drilling data 154 that is indicative of observed characteristics of the drilling of the well 106 at about 3:00 pm on Jan. 20, 2020. This may include measurements of operational drilling parameters, such as rate of penetration (ROP) of the drill bit 132, weight-on-bit (WOB), rotational speed of the drill string 130, and flowrate of drilling fluid circulating in the wellbore 120, and concentrations of surface gases ($C_1$ and $C_2$) collected by the drilling sensors 140 at about 3:00 pm on Jan. 10, 2020.

In some embodiments, method 200 includes determining a rock identification value based on the current well drilling data (block 208). This may include determining a ROCKID value by way of application of the current well drilling data obtained to the relationship of Equation 1 to determine a ROCKID value that is indicative of a type of rock currently engaged by a drill bit. For example, determining a rock identification value based on the current well drilling data may include the well control system 124 (or another operator of the well 106) applying measurements of operational drilling parameters associated with 3:00 pm on Jan. 20, 2020 while the drill bit 132 is located at a depth of 1,000 feet, such as rate of penetration (ROP) of the drill bit 132, weight-on-bit (WOB), rotational speed of the drill string 130, flowrate of drilling fluid circulating in the wellbore 120, and concentrations of surface gases ($C_1$ and $C_2$) collected by the drilling sensors 140 associated with 3:00 pm on Jan. 10, 2020, to Equation 1 to determine a ROCKID value of 5,020 that is associated with a depth of 1,000 feet in the wellbore 120.

In some embodiments, method 200 includes determining a rock type encountered based on the rock identification value (block 210). This may include determining a type of rock that corresponds to current ROCKID value based on a predetermined mapping of ROCKID values to type of rock. For example, determining a rock type encountered based on the rock identification value may include the well control system 124 (or another operator of the well 106) applying the ROCKID value of 5,020 (determined for 3:00 pm on Jan. 20, 2020 and a depth of 1,000 feet in the wellbore 120) to determine that the drill bit 132 is encountering rock of type B at 3:00 pm on Jan. 20, 2020 and at a depth of 1,000 feet in the wellbore 120 (e.g., based on the ROCKID value of 5,020 falling in the ROCKID range of 800-10,000 associated with rock type B).

In some embodiments, method 200 includes determining and conducting a drilling operation based on the rock type encountered (blocks 212 and 214). This may include determining drilling parameters for a subsequent phase of drilling based on the rock type encountered, and conducting a subsequent phase of the drilling operation in accordance with the determined drilling parameters. For example, in response to determining a rock type B (e.g., indicating that the drill bit 132 is currently engaged with rock type B within the formation 104), the well control system 124 (or another operator of the well 106) may decide to adjust one or more parameters of the ongoing drilling operation of well 106 (e.g., decide to slow a rotational speed of the drill string 130), and, in turn, control operation of the drilling system 122 in accordance with the adjusted operating parameters (e.g., control the drive system 136 to operate at a slower rotational speed). As a further example, in response to determining a rock type B (e.g., indicating that the drill bit 132 is currently engaged with rock type B within the formation 104), the well control system 124 (or another operator of the well 106) may decide to transition to a different phase or type of drilling operation (e.g., decide to inspect the drill bit or decide to transition to a coring operation), and, in turn, control operation of the drilling system 122 in accordance with the transition (e.g., control the drilling system 122 to conduct a POOH operation to inspect the drill bit 132, or control the drilling system 122 to conduct a POOH operation to change over to a coring-type drill bit 132 and return the drill string 130 into the wellbore 120 to conduct a coring-type drilling operation).

Figure 4:
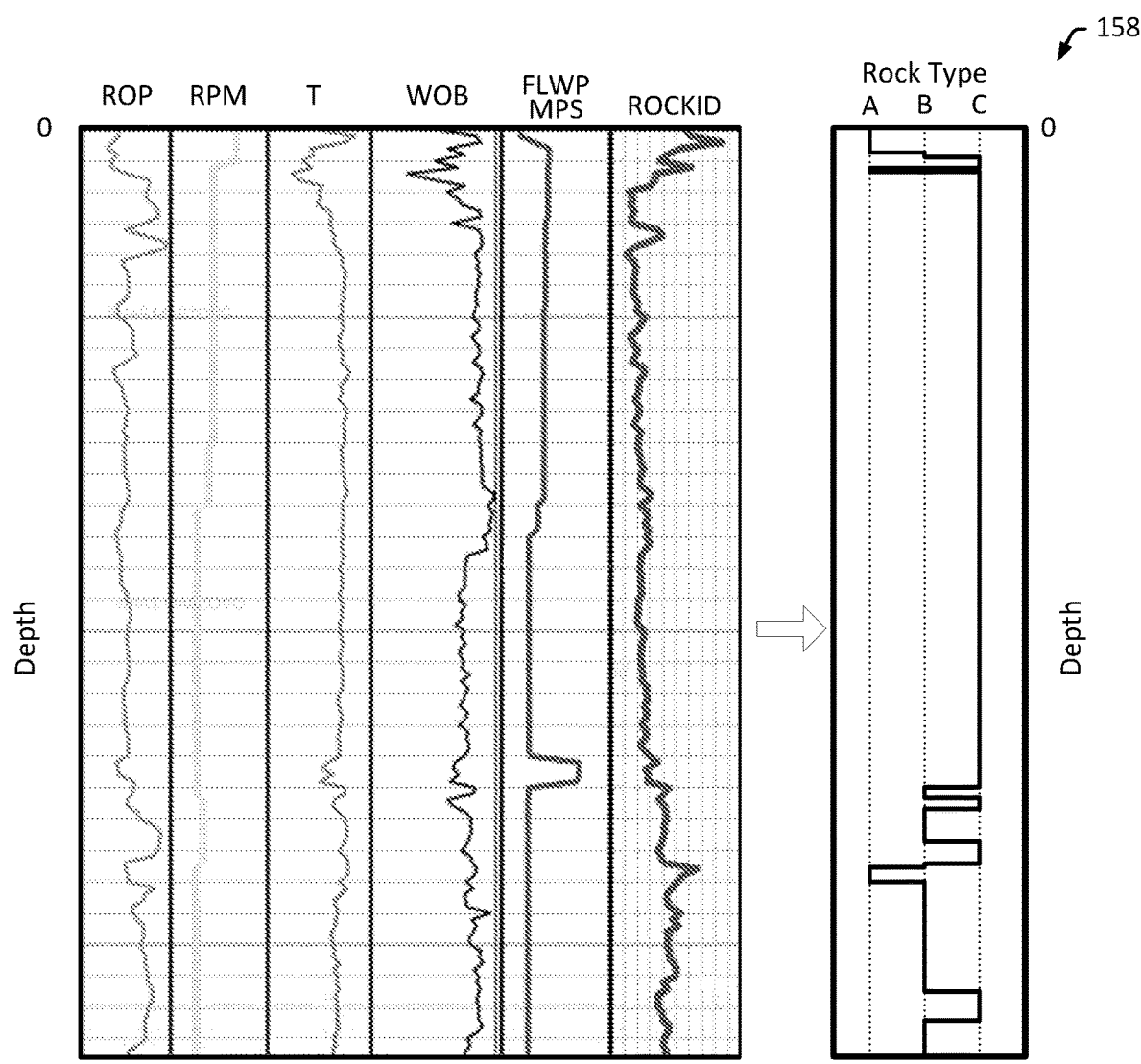
FIG. 4 is a diagram that illustrates a rock profile in accordance with one or more embodiments.

In some embodiments, the drilling operation assessment and control (e.g., blocks 206-214) may be repeated on regular basis (e.g., every minute, every 15 minutes, every 30 minutes, or hourly). This may provide for regular assessment and adjustment of drilling operations as drilling conditions dictate. FIG. 4 is a diagram that illustrates a rock profile 158 in accordance with one or more embodiments. In the illustrated embodiment, the rock profile 158 illustrates a profile of rock type (A, B, or C) versus depth, and profiles for corresponding ROCKIDs and associated ROP, RPM, T, FLWPMPS parameters versus depth. In some embodiments, the rock type mapping generation (e.g., block 202 and 204) may be performed on a regular basis (e.g., hourly, daily, weekly, monthly, or annually). This may provide for maintaining a rock type mapping that reflects updated well drilling data and associated observations.

Figure 5:
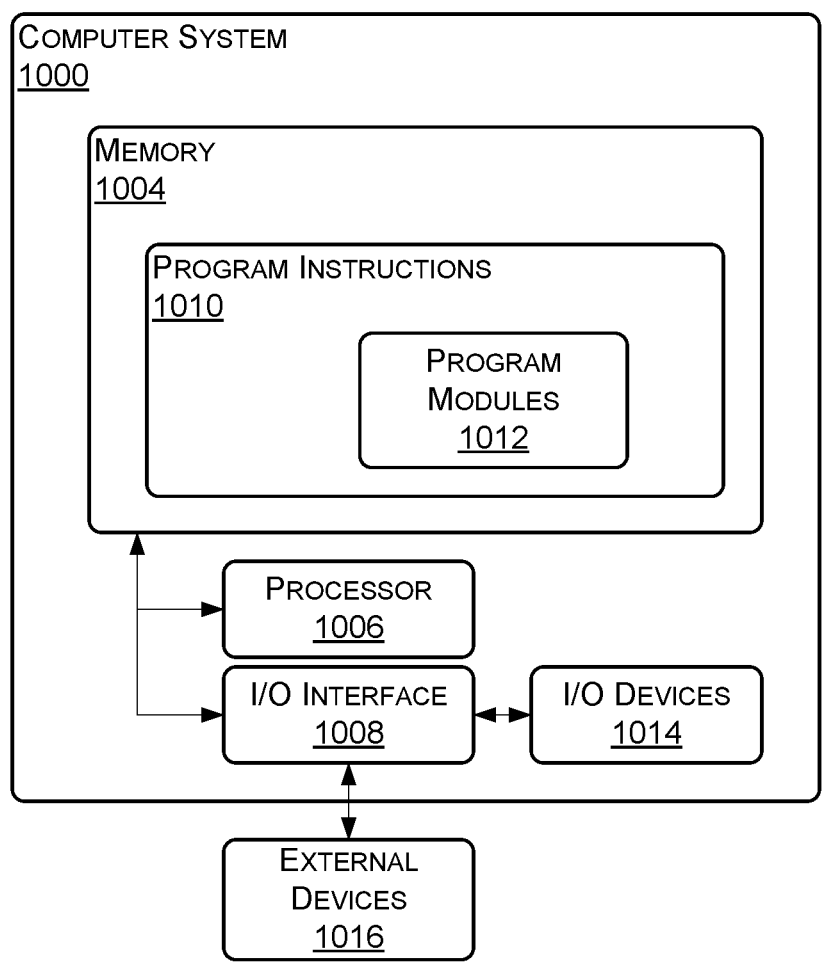
FIG. 5 is a diagram that illustrates an example computer system in accordance with one or more embodiments.

FIG. 5 is a diagram that illustrates an example computer system (or "system") 1000 in accordance with one or more embodiments. In some embodiments, the system 1000 is a programmable logic controller (PLC). The system 1000 may include a memory 1004, a processor 1006 and an input/output (I/O) interface 1008. The memory 1004 may include non-volatile memory (for example, flash memory, read-only memory (ROM), programmable read-only memory (PROM), erasable programmable read-only memory (EPROM), electrically erasable programmable read-only memory (EEPROM)), volatile memory (for example, random access memory (RAM), static random access memory (SRAM), synchronous dynamic RAM (SDRAM)), or bulk storage memory (for example, CD-ROM or DVD-ROM, hard drives). The memory 1004 may include a non-transitory computer-readable storage medium having program instructions 1010 stored thereon. The program instructions 1010 may include program modules 1012 that are executable by a computer processor (for example, the processor 1006) to cause the functional operations described, such as those described with regard to the well control system 124 (or another operator of the well 106), or the method 200.

The processor 1006 may be any suitable processor capable of executing program instructions. The processor 1006 may include a central processing unit (CPU) that carries out program instructions (for example, the program instructions of the program modules 1012) to perform the arithmetical, logical, or input/output operations described. The processor 1006 may include one or more processors. The I/O interface 1008 may provide an interface for communication with one or more I/O devices 1014, such as a joystick, a computer mouse, a keyboard, or a display screen (for example, an electronic display for displaying a graphical user interface (GUI)). The I/O devices 1014 may include one or more of the user input devices. The I/O devices 1014 may be connected to the I/O interface 1008 by way of a wired connection (for example, an Industrial Ethernet connection) or a wireless connection (for example, a Wi-Fi connection). The I/O interface 1008 may provide an interface for communication with one or more external devices 1016. In some embodiments, the I/O interface 1008 includes one or both of an antenna and a transceiver. The external devices 1016 may include, for example, devices of the drilling system 122.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims. Headings used here are for organizational purposes only and are not meant to be used to limit the scope of the description.

It will be appreciated that the processes and methods described here are example embodiments of processes and methods that may be employed in accordance with the techniques described here. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (that is, meaning having the potential to), rather than the mandatory sense (that is, meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (for example, by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A hydrocarbon well drilling system, comprising:
a well drilling system configured to drill a wellbore of a hydrocarbon well into a subsurface formation, the well drilling system comprising:
a drill string comprising:
a drill bit;
drill pipe; and
drilling sensors configured to sense characteristics of a drilling operation conducted by the well drilling system;
a well control system configured to perform the following operations:
obtaining, by way of the drilling sensors, drilling data that is indicative of characteristics of the drilling operation, the drilling data comprising:
rate of penetration data that is indicative of rate of penetration of the drill bit into the subsurface formation;
weight on bit data that is indicative of weight acting on the drill bit;
rotation data that is indicative of rotational speed of the drill pipe;
torque data that is indicative of a torque acting on the drill pipe;
fluid circulation data that is indicative of rate of drilling fluid circulation;
surface gas data that is indicative of concentrations of one or more surface gases produced;
determining, based on the drilling data, the following drilling characteristics for a given point in time:
an observed rate of penetration of the drill bit at the given point in time ($ROP_i$) determined based on the rate of penetration data,
a product of observed concentrations of one or more surface gases produced at the given point in time ($C_{prod_i}$) determined based on the surface gas data;
a sum of observed concentrations of one or more surface gases produced at the given point in time ($C_{sum_i}$) determined based on the surface gas data;
an observed weight acting on the drill bit at the given point in time ($WOB_i$ determined based on the weight on bit data;
an observed torque acting on the drill pipe at the given point in time ($T_i$) is determined based on the torque data;
an observed rotational speed of the drill pipe at the given point in time ($RPM_i$) determined based on the rotation data; and
an observed rate of drilling fluid circulation at the given point in time ($FLWPMPS_i$) determined based on the fluid circulation data;
applying the drilling data to the following rock identification relationship to determine a rock identification value ($ROCKID_i$) that is indicative of a type of rock engaged by the drill bit at the given point in time:

$$ROCKID_i = \frac{B * \left(\log_{10}\left(\frac{ROP_i}{ROPB_i}\right)\right) * C_{prod_i}}{(C_{sum_i} * A)} * \frac{WOB_i * T_i * RPM_i * FLWPMPS_i}{DCF}$$

where:
$ROPB_i$ is a base rate of penetration of the drill bit,
DCF is a drilling calibration factor, and
A and B are calibration constants associated with the subsurface formation;
determining, based on the $ROCKID_i$, a type of rock engaged by the drill bit at the given point in time;
determining, based on the type of rock determined, a drilling operation parameter; and
conducting a drilling operation in accordance with the drilling operation parameter.

2. The system of claim 1, the operations further comprising:
determining a rock type mapping that maps ROCKID values to associated types of rocks,
wherein the rock type mapping maps the $ROCKID_i$ to the type of rock, and
wherein the type of rock engaged by the drill bit at the given point in time is determined based the mapping of the $ROCKID_i$ to the type of rock.

3. The system of claim 2, wherein determining a rock type mapping comprises:
identifying drilling parameters associated with known rock types;
applying the drilling parameters associated with known rock types to the rock identification relationship to generate ROCKID values; and
associating, based on the ROCKID values generated and the associated known rock types, groups of ROCKID values with respective ones of the known rock types.

4. The system of claim 1, the operations further comprising determining the drilling calibration factor (DCF) based on a comparison of determined ROCKID values for one or more points in time to known types of rocks encountered during drilling at the one or more points in time.

5. The system of claim 4, wherein the known types of rocks encountered during drilling at the one or more points in time are determined based on inspection of formation rock encountered by the drill bit at the one or more points in time.

6. The system of claim 5, wherein the inspection comprises physical inspection of one or more samples of rock extracted from the location of the drill bit at the one or more points in time.

7. The system of claim 5, wherein the inspection comprises inspection of well logs of a depth interval that comprises the location of the drill bit at the one or more points in time.

8. The system of claim 1, wherein the drilling operation parameter comprises a time to conduct a pull out of hole operation to inspect the drill bit, and wherein conducting a drilling operation in accordance with the drilling operation parameter comprises conducting the pull out of hole operation to inspect the drill bit.

9. The system of claim 1, wherein the drilling operation parameter comprises a time to conduct a coring operation, and wherein conducting a drilling operation in accordance with the drilling operation parameter comprises conducting the coring operation.

10. A method of drilling a hydrocarbon well, the method comprising:
  obtaining, by way of the drilling sensors, drilling data that is indicative of characteristics of drilling a wellbore of a hydrocarbon well into a subsurface formation by way of a drilling system that includes a drill string that comprises a drill bit, drill pipe and the drilling sensors, the drilling data comprising:
    rate of penetration data that is indicative of rate of penetration of the drill bit into the subsurface formation;
    weight on bit data that is indicative of weight acting on the drill bit;
    rotation data that is indicative of rotational speed of the drill pipe;
    torque data that is indicative of a torque acting on the drill pipe;
    fluid circulation data that is indicative of rate of drilling fluid circulation;
    surface gas data that is indicative of concentrations of one or more surface gases produced;
  determining, based on the drilling data, the following drilling characteristics for a given point in time:
    an observed rate of penetration of the drill bit at the given point in time ($ROP_i$) determined based on the rate of penetration data;
    a product of observed concentrations of one or more surface gases produced at the given point in time ($C_{prod_i}$) determined based on the surface gas data;
    a sum of observed concentrations of one or more surface gases produced at the given point in time ($C_{sum_i}$) determined based on the surface gas data;
    an observed weight acting on the drill bit at the given point in time ($WOB_i$) determined based on the weight on bit data;
    an observed torque acting on the drill pipe at the given point in time ($T_i$) is determined based on the torque data;
    an observed rotational speed of the drill pipe at the given point in time ($RPM_i$) determined based on the rotation data; and
    an observed rate of drilling fluid circulation at the given point in time ($FLWPMPS_i$) determined based on the fluid circulation data;
  applying the drilling data to the following rock identification relationship to determine a rock identification value ($ROCKID_i$) that is indicative of a type of rock engaged by the drill bit at the given point in time:

$$ROCKID_i = \frac{B * \left(\log_{10}\left(\frac{ROP_i}{ROPB_i}\right)\right) * C_{prod_i}}{(C_{sum_i} * A)} * \frac{WOB_i * T_i * RPM_i * FLWPMPS_i}{DCF}$$

where:
    $ROPB_i$ is a base rate of penetration of the drill bit,
    DCF is a drilling calibration factor, and
    A and B are calibration constants associated with the subsurface formation;
  determining, based on the $ROCKID_i$, a type of rock engaged by the drill bit at the given point in time;
  determining, based on the type of rock determined, a drilling operation parameter; and
  conducting a drilling operation in accordance with the drilling operation parameter.

11. The method of claim 10, further comprising:
  determining a rock type mapping that maps ROCKID values to associated types of rocks,
  wherein the rock type mapping maps the $ROCKID_i$ to the type of rock, and
  wherein the type of rock engaged by the drill bit at the given point in time is determined based the mapping of the $ROCKID_i$ to the type of rock.

12. The method of claim 11, wherein determining a rock type mapping comprises:
  identifying drilling parameters associated with known rock types;
  applying the drilling parameters associated with known rock types to the rock identification relationship to generate ROCKID values; and
  associating, based on the ROCKID values generated and the associated known rock types, groups of ROCKID values with respective ones of the known rock types.

13. The method of claim 10, further comprising determining the drilling calibration factor (DCF) based on a comparison of determined ROCKID values for one or more points in time to known types of rocks encountered during drilling at the one or more points in time.

14. The method of claim 13, wherein the known types of rocks encountered during drilling at the one or more points in time are determined based on inspection of formation rock encountered by the drill bit at the one or more points in time.

15. The method of claim 14, wherein the inspection comprises physical inspection of one or more samples of rock extracted from the location of the drill bit at the one or more points in time.

16. The method of claim 14, wherein the inspection comprises inspection of well logs of a depth interval that comprises the location of the drill bit at the one or more points in time.

17. The method of claim 10, wherein the drilling operation parameter comprises a time to conduct a pull out of hole operation to inspect the drill bit, and wherein conducting a drilling operation in accordance with the drilling operation parameter comprises conducting the pull out of hole operation to inspect the drill bit.

18. The method of claim 10, wherein the drilling operation parameter comprises a time to conduct a coring operation, and wherein conducting a drilling operation in accordance with the drilling operation parameter comprises conducting the coring operation.

19. Non-transitory computer readable storage medium comprising program instructions stored thereon that are executable by a computer processer to perform the following operations for drilling a hydrocarbon well:
obtaining, by way of drilling sensors, drilling data that is indicative of characteristics of drilling a wellbore of a hydrocarbon well into a subsurface formation by way of a drilling system that includes a drill string that comprises a drill bit, drill pipe and
the drilling sensors, the drilling data comprising:
rate of penetration data that is indicative of rate of penetration of the drill bit into the subsurface formation;
weight on bit data that is indicative of weight acting on the drill bit;
rotation data that is indicative of rotational speed of the drill pipe;
torque data that is indicative of a torque acting on the drill pipe;
fluid circulation data that is indicative of rate of drilling fluid circulation;
surface gas data that is indicative of concentrations of one or more surface gases produced;
determining, based on the drilling data, the following drilling characteristics for a given point in time:
an observed rate of penetration of the drill bit at the given point in time ($ROP_i$) determined based on the rate of penetration data,
a product of observed concentrations of one or more surface gases produced at the given point in time ($C_{prod_i}$) determined based on the surface gas data;
a sum of observed concentrations of one or more surface gases produced at the given point in time ($C_{sum_i}$) determined based on the surface gas data;
an observed weight acting on the drill bit at the given point in time ($WOB_i$) determined based on the weight on bit data;
an observed torque acting on the drill pipe at the given point in time ($T_i$) is determined based on the torque data;
an observed rotational speed of the drill pipe at the given point in time ($RPM_i$) determined based on the rotation data; and
an observed rate of drilling fluid circulation at the given point in time ($FLWPMPS_i$) determined based on the fluid circulation data;
applying the drilling data to the following rock identification relationship to determine a rock identification value ($ROCKID_i$) that is indicative of a type of rock engaged by the drill bit at the given point in time:

$$ROCKID_i = \frac{B*\left(\log_{10}\left(\frac{ROP_i}{ROPB_i}\right)\right)*C_{prod_i}}{(C_{sum_i}*A)} * \frac{WOB_i*T_i*RPM_i*FLWPMPS_i}{DCF}$$

where:
$ROPB_i$ is a base rate of penetration of the drill bit,
DCF is a drilling calibration factor, and
A and B are calibration constants associated with the subsurface formation;
determining, based on the $ROCKID_i$, a type of rock engaged by the drill bit at the given point in time;
determining, based on the type of rock determined, a drilling operation parameter; and
conducting a drilling operation in accordance with the drilling operation parameter.

20. The medium of claim 19, the operations further comprising:
determining a rock type mapping that maps ROCKID values to associated types of rocks,
wherein the rock type mapping maps the $ROCKID_i$ to the type of rock, and
wherein the type of rock engaged by the drill bit at the given point in time is determined based the mapping of the $ROCKID_i$ to the type of rock.

21. The medium of claim 20, wherein determining a rock type mapping comprises:
identifying drilling parameters associated with known rock types;
applying the drilling parameters associated with known rock types to the rock identification relationship to generate ROCKID values; and
associating, based on the ROCKID values generated and the associated known rock types, groups of ROCKID values with respective ones of the known rock types.

22. The medium of claim 19, the operations further comprising:
determining the drilling calibration factor (DCF) based on a comparison of determined ROCKID values for one or more points in time to known types of rocks encountered during drilling at the one or more points in time.

23. The medium of claim 22, wherein the known types of rocks encountered during drilling at the one or more points in time are determined based on inspection of formation rock encountered by the drill bit at the one or more points in time.

24. The medium of claim 23, wherein the inspection comprises physical inspection of one or more samples of rock extracted from the location of the drill bit at the one or more points in time.

25. The medium of claim 23, wherein the inspection comprises inspection of well logs of a depth interval that comprises the location of the drill bit at the one or more points in time.

26. The medium of claim 19, wherein the drilling operation parameter comprises a time to conduct a pull out of hole operation to inspect the drill bit, and wherein conducting a drilling operation in accordance with the drilling operation parameter comprises conducting the pull out of hole operation to inspect the drill bit.

27. The medium of claim 19, wherein the drilling operation parameter comprises a time to conduct a coring operation, and wherein conducting a drilling operation in accordance with the drilling operation parameter comprises conducting the coring operation.

* * * * *